US00PP13888P39

(12) United States Plant Patent
White

(10) Patent No.: US PP13,888 P3
(45) Date of Patent: Jun. 17, 2003

(54) APPLE TREE NAMED 'SCIFRESH'

(75) Inventor: Allan G White, Havelock North (NZ)

(73) Assignee: The Horticulture and Food Research Institute of New Zealand Limited, Palmerston North (NZ)

( * ) Notice: Subject to any disclaimer, the term of this patent is extended or adjusted under 35 U.S.C. 154(b) by 68 days.

(21) Appl. No.: 09/834,757

(22) Filed: Apr. 13, 2001

(65) Prior Publication Data

US 2002/0152519 P1 Oct. 17, 2002

(51) Int. Cl.[7] ..... A01H 5/00
(52) U.S. Cl. ..... Plt./161
(58) Field of Search ..... Plt./161

(56) References Cited

U.S. PATENT DOCUMENTS

PP4,121 P 10/1977 Hove et al. ..... Plt./161
PP11,604 P * 10/2000 Easton ..... Plt./161

OTHER PUBLICATIONS

UPOV–ROM Plant Variety Database, GTI Jouve Retrieval Software, 2002/03.*
New Zealand Plant Variety Rights Journal, No. 71, Jul.–Sep. 1997, Published: 14 Oct. 14, 1997, p. 3, item 14.

* cited by examiner

*Primary Examiner*—Bruce R. Campell
*Assistant Examiner*—Anne Marie Grünberg
(74) *Attorney, Agent, or Firm*—Greenlee, Winner and Sullivan, P.C.

(57) ABSTRACT

A new and distinct apple variety is described. The variety results from selection among a population of seedlings derived from crossing the apple varieties known as 'Braeburn' (not patented) and 'Royal Gala' (U.S. Plant Pat. No. 4,121). The fruit of the apple tree of this new variety has an attractive appearance characterised by its striped colour pattern and is notable for its excellent eating quality post-storage. The new variety matures for harvest between the parent varieties and has been named 'Scifresh'.

4 Drawing Sheets

BACKGROUND OF THE INVENTION

The invention described herein is a new variety of apple tree (*Malus domestica*). The new variety was selected from a population of seedlings derived from crossing the apple varieties 'Braeburn' (not patented) and 'Royal Gala' (U.S. Plant Pat. No 4,121). The cross was made in 1985 on trees at Goddard Lane, Havelock North, Hawkes Bay, New Zealand. The new variety was determined to be distinct from the parent varieties 'Braeburn' and 'Royal Gala', as well as the sibling varieties 'Scigold' (not patented) and the variety 'Mariri Red' (U.S. Plant Pat. No. 11,604), and 'Sweetie' (not patented), by the following characteristics:

'Braeburn': 'Scifresh' has an earlier harvest season by at least a week, smaller fruit size, and the fruit shape is globose rather than conical, while fruit colour is a lighter red.

'Royal Gala': 'Scifresh' has a later harvest season, firmer flesh, and longer storage life.

'Scigold': 'Scifresh' fruit colour is red striped (whereas 'Scigold' is yellow-green), and has firmer flesh.

'Sweetie': 'Scifresh' has a later harvest season, more globose shape, and smaller fruit size.

'Mariri Red': 'Scifresh' has an earlier harvest season, being mature one week before 'Braeburn', whereas 'Mariri Red' is mature one week after Braeburn. 'Scifresh' has bright red striped fruit (75% coverage of greyed-red stripes over red on a yellow background), whereas 'Mariri Red' has dark red blushed fruit (almost 100% coverage of greyed-purple (R.H.S.C.C. 187B) blush on a yellow-green (R.H.S.C.C. 150C) background).

The new variety has been named 'Scifresh'. Asexual propagation by budding shows that the unique combination of characteristics of the variety come true to form and are established and transmitted through succeeding propagation. In order to obtain true-to-type clones of the initial plant, the breeders asexually propagated plants by budding dormant buds from the original seedling onto MM.106 rootstock. The plants were asexually reproduced at Goddard Lane, Havelock North, Hawkes Bay, New Zealand.

SUMMARY OF THE INVENTION

The new variety produces fruit with an attractive striped colour pattern and is notable for its excellent eating quality post-storage.

BRIEF DESCRIPTION OF DRAWINGS

The accompanying photographs show typical specimens of the tree, foliage and fruit of the new variety as depicted in colours as nearly true as is reasonably possible to make the same in a colour illustration of this character.

DETAILED DESCRIPTION

Figure 1:
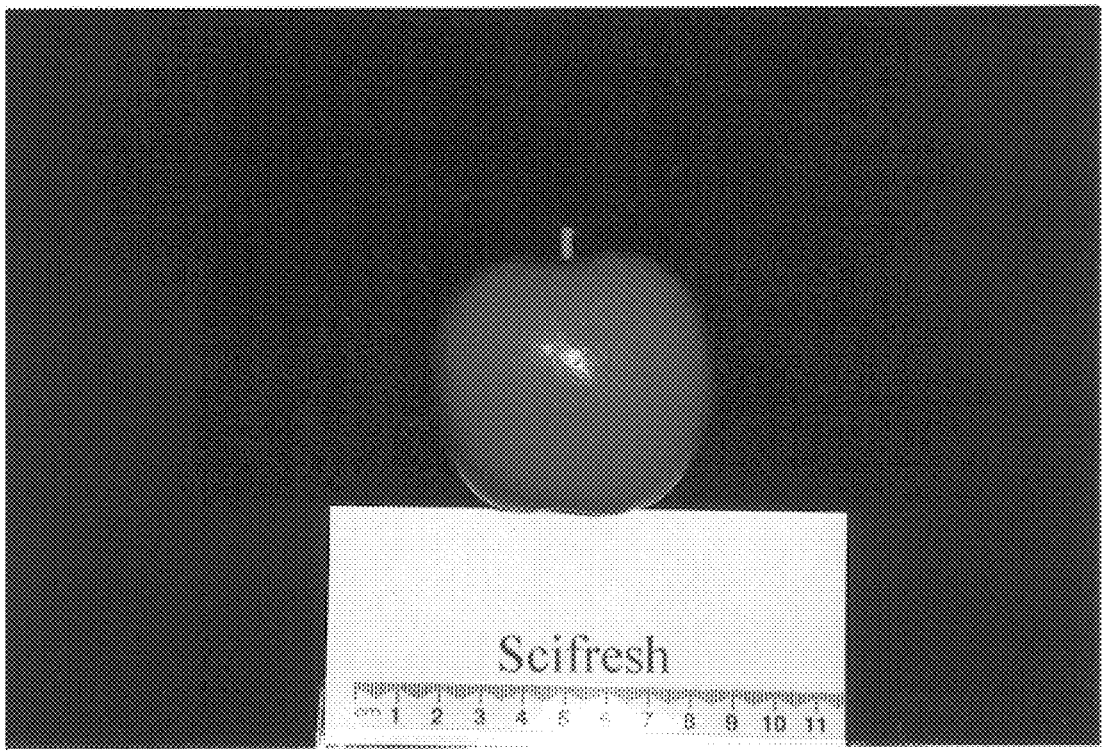
FIG. 1: side view of a typical fruit of the apple variety 'Scifresh'.
Figure 2:
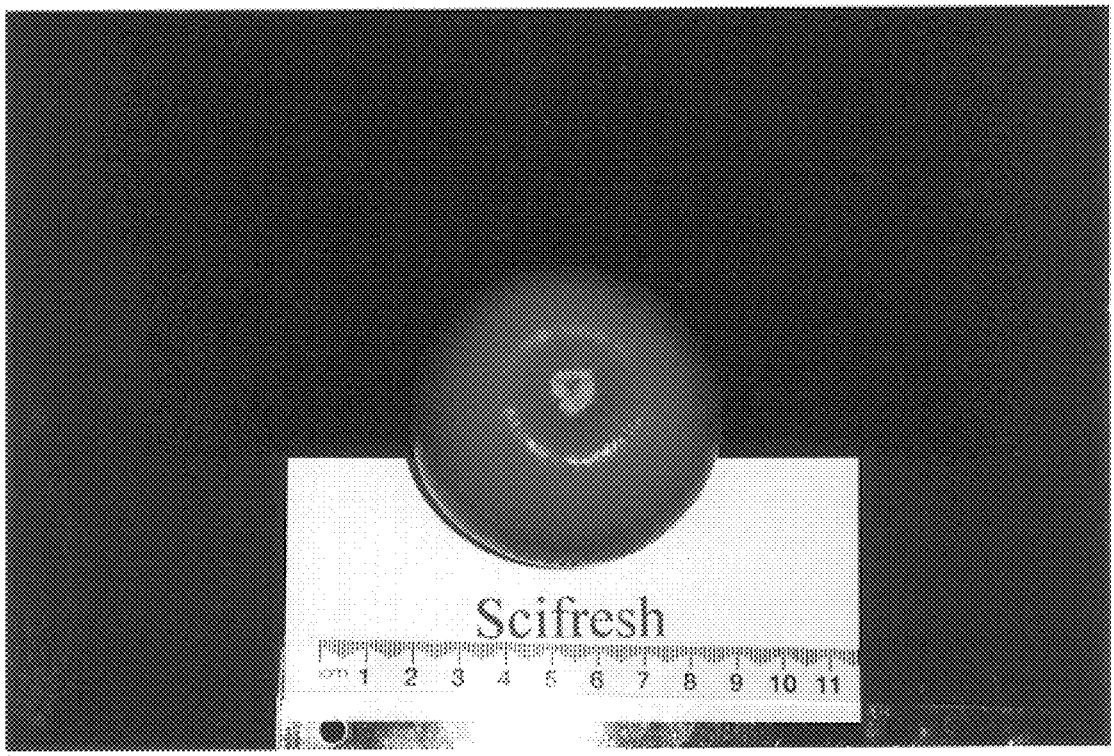
FIG. 2: calyx end view of a typical fruit of the apple variety 'Scifresh'.
Figure 3:
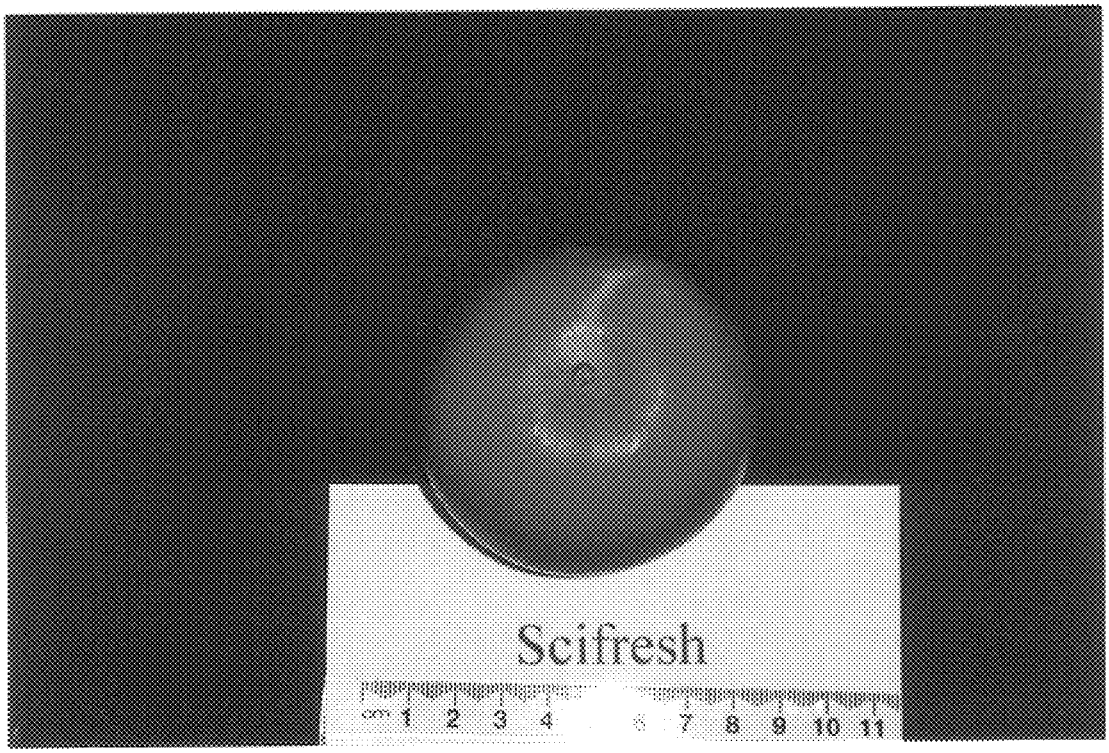
FIG. 3: stem end view of a typical fruit of the apple variety 'Scifresh'.
Figure 4:
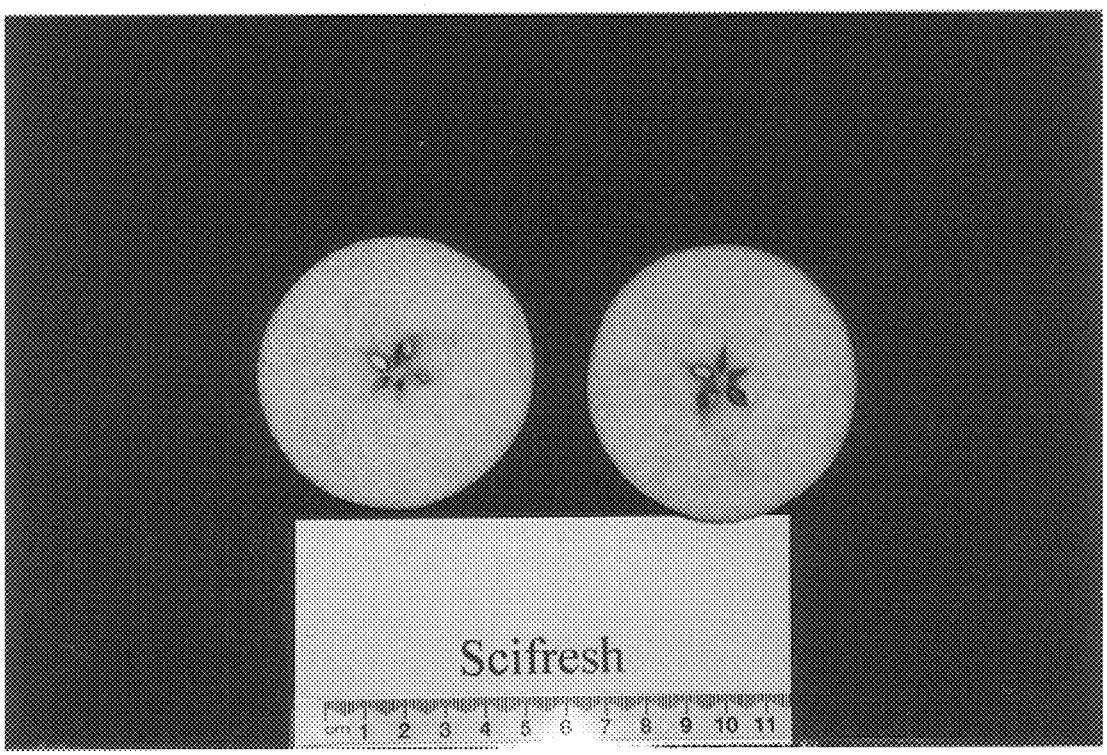
FIG. 4: cross sectional view of a typical fruit of the apple variety 'Scifresh'.
Figure 5:
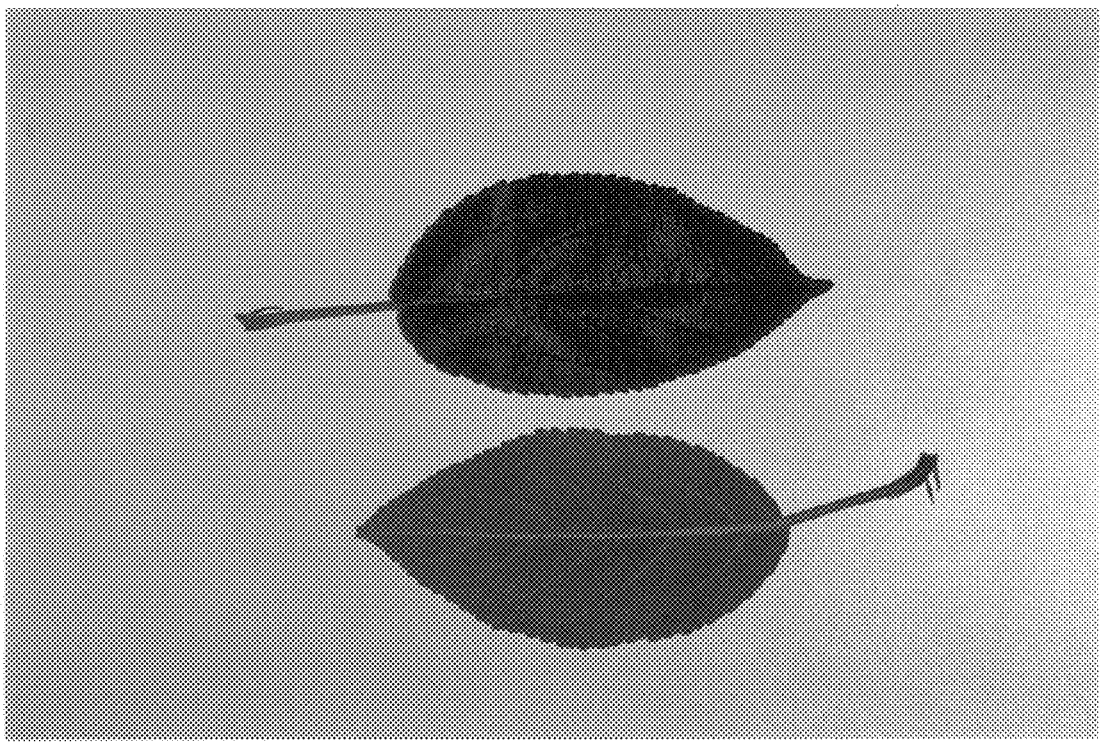
FIG. 5: two typical mature leaves of the variety 'Scifresh' showing the upper and lower surfaces.
Figure 6:
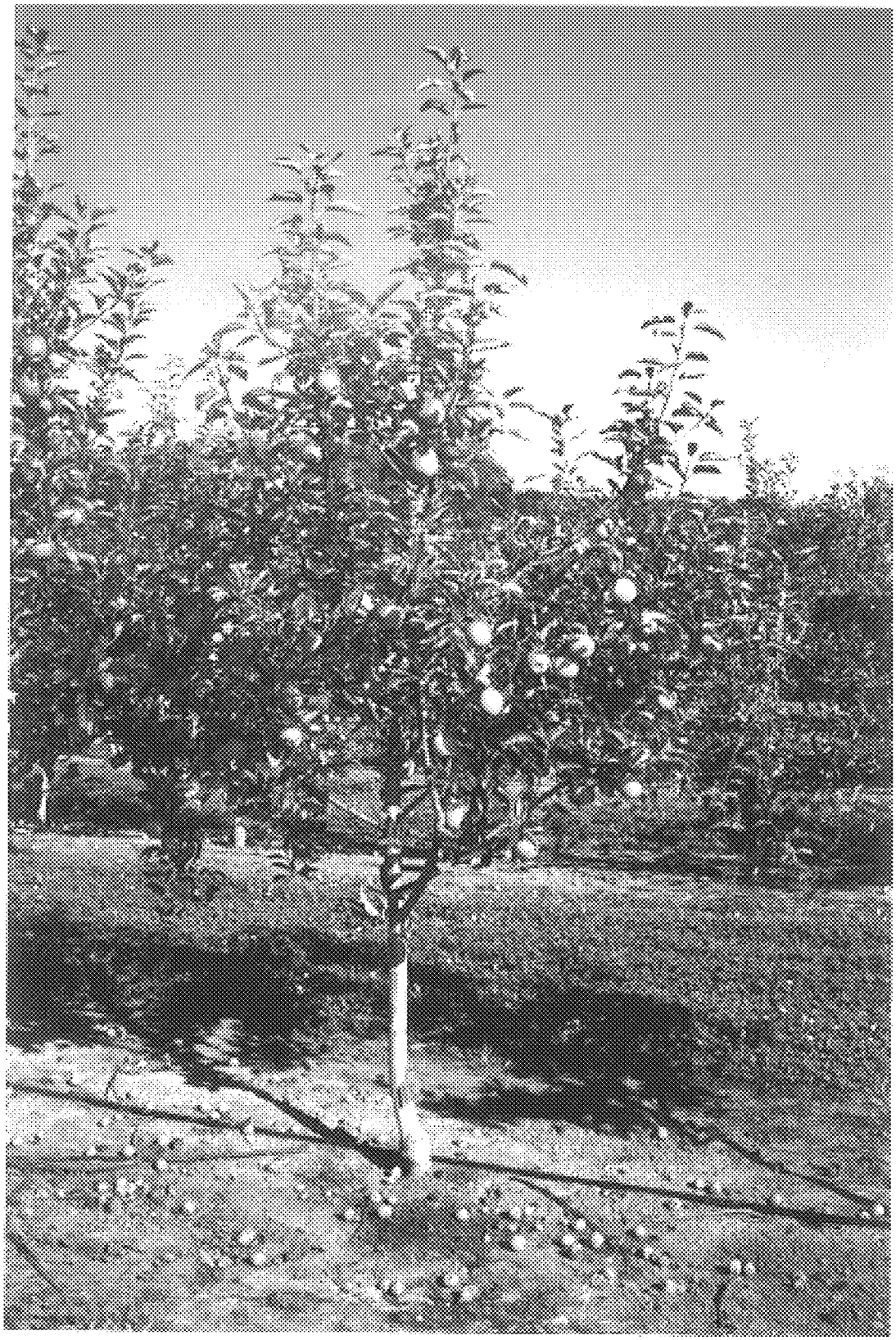
FIG. 6: tree of the variety 'Scifresh' showing canopy and crop development prior to harvest.

The following is a detailed description of the new variety with colour terminology in accordance with The Royal Horticultural Society Colour Charts (R.H.S.C.C.) 1986 edition.

The specimens described were grown at Havelock North, Hawkes Bay, New Zealand. The observations were made in the 2000–2001 season on trees on MM.106 rootstock that were three years old at the time, and managed under standard orchard practice.

Tree: Medium size; spreading habit; bearing on spurs; medium vigour on MM.106 rootstock. Four-year-old trees grown on MM.106 rootstock and managed by winter pruning are 2.5 metres high and 2.2 metres wide at a point 1 metre above the graft union.

Trunk: Moderately rough; diameter 45 mm at a height of 200 mm; the bark is grey-green R.H.S.C.C. 197C when mature.

Branches: Thin; moderately rough; moderate branching, the angle of branching being typically 20 degrees above the horizontal; approximately 6 spurs per 100 mm of growth on two year old wood; length of annual growth 300–400 mm.

Bark lenticels: Medium size, being 1.0 mm wide by 1.5 mm long on one-year-old wood and 2.5 mm wide by 1.0 mm long on three-year-old wood; distributed at a density of 7 per square centimetre. Lenticel colour is grey-yellow (R.H.S.C.C. 161B).

Leaves: Length 91 mm; width 50 mm; upward pose; upfolded to concave shape in cross section; serrate indentations of margin; medium glossiness on upper surface; weak pubescence on lower side; petiole length 23–25 mm; stipule size 6 mm by 1 mm on average; medium time of bud burst; Colour of immature leaves is yellow-green (R.H.S.C.C. 146A) on the upper surface, and green (R.H.S.C.C. 138A) on the lower surface. Mature leaf colour is R.H.S.C.C. 147A (yellow-green) on the upper surface and R.H.S.C.C. 138A (green) on the lower surface. Leaf veins are coloured R.H.S.C.C. 148D (yellow-green) on the upper surface and R.H.S.C.C. 144D (yellow-green) on the lower surface.

Flower buds: Medium size, 12 mm long; red-purple R.H.S.C.C. 63B at popcorn stage.

Flowers: Medium blooming period, starting about October 5 for 2 weeks; five petals not touching, colour red R.H.S.C.C. 55B fading to white on both sides, 17 mm long by 10 mm wide; five sepals 7 mm long by 3.5 mm wide, pointed, yellow-green R.H.S.C.C. 144D with orange-red R.H.S.C.C. 34A tips; many stamens with white (R.H.S.C.C. 155A) filaments of 5 mm long and yellow R.H.S.C.C. 11B anthers that are 1.5 mm long by 0.5 mm wide; stigmatic surface typically at same level as anthers, stigmas 8 mm long, and of yellow-green colour R.H.S.C.C. 151C; pubescent ovary; slight fragrance; flower size when open 38 mm in diameter.

Fruit: Examined at optimum. Harvest period is from about March 12 until March 30 in Hawkes Bay, New Zealand.

Fruit size: Small to medium; average width, 72 mm; average height, 65 mm; average weight, 177 g.

Fruit shape: Ranges from short globose to conical; symmetrical in side view; ribbing absent; medium degree of crowning at distil end.

Fruit cavity: Average width, 27 mm; average depth, 11 mm.

Fruit basin: Average width, 23 mm; average depth, 9 mm.

Fruit stem: Medium thickness; medium length, 22 mm.

Fruit sepal: Medium length, 7 mm long by 3.5 mm wide; spacing, touching.

Fruit eye: Size, average 7 mm diameter; aperture, closed.

Fruit skin: Smooth; bloom of skin, absent; greasiness of skin, slight; cracking tendency of skin, absent; thickness, medium; background colour, yellow-green R.H.S.C.C. 154B; lenticels, small.

Fruit over colour: Approximately 75% of skin surface; red R.H.S.C.C. 42C overlain with 1 mm to 2.5 mm wide stripes of greyed-red R.H.S.C.C. 179A; absent to low amount of russet around stem cavity.

Fruit background colour: Yellow R.H.S.C.C. 8A

Fruit flesh: Firm (9.2 kgF), juicy and crisp; yellow-white R.H.S.C.C. 158A.

Fruit texture: Medium crispness.

Fruit flavour: At harvest maturity, medium sweetness of 12% brix; medium titratable acidity of 0.6% malic acid; rich aroma.

Fruit quality: Excellent.

Fruit sinus: Closed.

Seeds: Five locules of 14.5 mm long by 7 mm wide; 1 to 2 seeds per locule; medium seed size of 10 mm long by 5 mm wide; colour, greyed orange R.H.S.C.C. 175A.

Use: Dessert.

Keeping quality: Excellent eating quality for at least 5 months in refrigerated air storage at 0° C. After 150 days storage at 0° C. followed by seven days at ambient temperature, flesh firmness was 7.6 kgF, sweetness was 14.3% brix, and acidity 0.41% malic acid.

Production: Mid season, regular cropping.

Management: Thinning of crop load in early summer is recommended. Minimal pruning is required as the trees have a wide spreading habit. Cross-pollination is required—any other diploid apple cultivar that flowers at a similar time is a suitable polleniser. Scifresh does not have pest or disease resistance that differs from other commercial cultivars of apple.

We claim:

1. A new and distinct variety of apple plant, *Malus domestica*, substantially as herein shown and described.

* * * * *